United States Patent [19]

Shibata et al.

[11] Patent Number: 4,915,815
[45] Date of Patent: Apr. 10, 1990

[54] SENSOR INCORPORATING A HEATER

[75] Inventors: Kazuyoshi Shibata; Yoshihiko Mizutani, both of Nagoya, Japan

[73] Assignee: NGK Insulators, Ltd., Japan

[21] Appl. No.: 185,315

[22] Filed: Apr. 20, 1988

Related U.S. Application Data

[63] Continuation of Ser. No. 919,433, Oct. 16, 1986, abandoned.

[30] Foreign Application Priority Data

Oct. 18, 1985 [JP] Japan .................. 60-234047

[51] Int. Cl.<sup>4</sup> .......................................... G01N 27/58
[52] U.S. Cl. ......................................... 204/429; 204/428
[58] Field of Search .................. 204/406, 421, 425–429

[56] References Cited

U.S. PATENT DOCUMENTS

| 4,629,549 | 12/1986 | Kojima et al. | 204/406 |
| 4,639,305 | 1/1987 | Shibata et al. | 204/425 |
| 4,642,174 | 2/1987 | Shibata | 204/425 |
| 4,647,364 | 3/1987 | Mase et al. | 204/425 |

FOREIGN PATENT DOCUMENTS

| 0019636 | 12/1980 | European Pat. Off. |
| 0087626 | 9/1983 | European Pat. Off. |
| 0108179 | 5/1984 | European Pat. Off. |
| 0142993 | 5/1985 | European Pat. Off. |
| 2046921 | 11/1980 | United Kingdom |
| 2054868 | 2/1981 | United Kingdom |

Primary Examiner—John F. Niebling
Assistant Examiner—Ben C. Hsing
Attorney, Agent, or Firm—Arnold, White & Durkee

[57] ABSTRACT

A heater-built-in sensor for detecting a component in a measurement gas, including an electrochemical cell having a solid electrolyte body, and a pair of electrodes formed on the solid electrolyte body, a heater for heating at least a detecting portion of the cell which includes the measuring electrode, and a protective covering device disposed around the detecting portion. The covering device includes a gas-inlet portion for introducing the measurement gas to the measuring electrode, and a thermally insulating portion for preventing dissipation of a heat generated by the heater. The thermally insulating portion, which is separated from the gas-inlet portion, is adapted to surround the detecting portion so as to prevent the measurement gas from flowing to and from any parts of the detecting portion, except a part at which the measuring electrode is located.

48 Claims, 5 Drawing Sheets

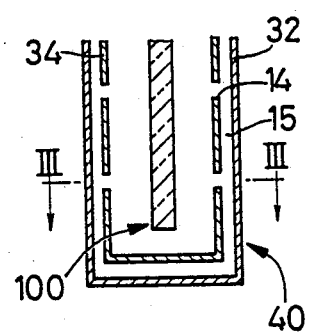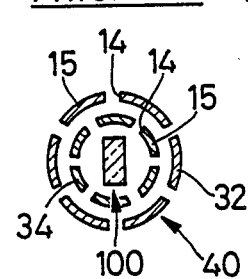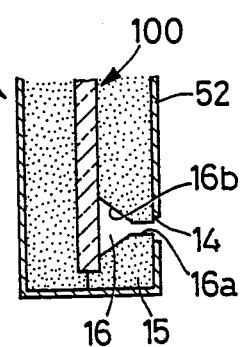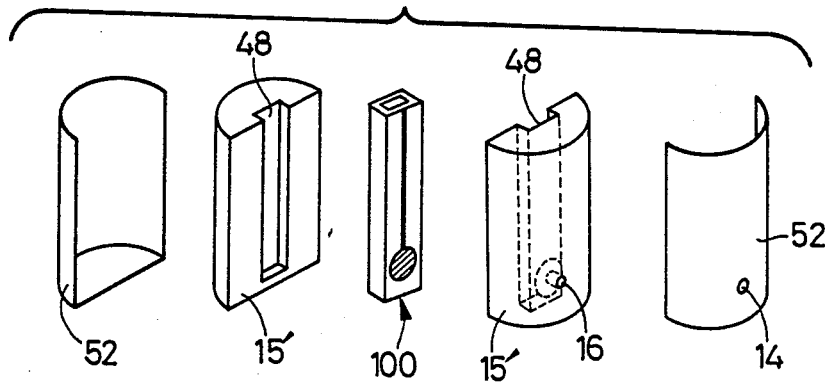

SENSOR INCORPORATING A HEATER

This is a continuation of application Ser. No. 919,433, filed Oct. 16, 1986, now abandoned.

BACKGROUND OF THE INVENTION

1. Field of the Invention

The present invention relates generally to the construction of a sensor incorporating a heater, and more particularly to a sensor which has thermally insulating means for preventing dissipation or transfer of heat generated by heating means incorporated therein, and gas-inlet means for introducing a measurement gas to a detecting portion which has a measuring electrode.

2. Discussion of the Prior Art

An oxygen sensor using an electrochemical element or cell having a tubular solid electrolyte body is known, for example, in the field of controlling an amount of oxygen contained in an exhaust gas emitted from an internal combustion engine. The tubular solid electrolyte body is closed at its one end, and has a pair of electrodes on substantially the entire areas of its opposite inner and outer surfaces. In this type of oxygen sensor, a protective covering member is provided so as to surround the detecting end portion of the electrochemical cell, to protect the sensor from contamination by foreign substances contained in the exhaust gas, or from mechanical damages during installation of the sensor. Such a protective covering member has apertures or openings formed over its entire area, so that the entire area of the measuring electrode formed on the outer surface of the tubular solid electrolyte body may be evenly exposed to the measurement gas, and so that the electrochemical cell may be effectively heated by the hot exhaust gas to a suitable operating temperature.

However, such an oxygen sensor suffers from a drawback that immediately after a cold engine is started, the temperature of the exhaust gas is not high enough to heat the electrochemical cell to a sufficiently high operating temperature, and therefore the electrochemical cell cannot operate in a reliable manner until the exhaust gas has become sufficiently hot.

To solve the above drawback, it is known to provide an oxygen sensor with suitable heating means such as an electric heater, which is disposed in direct or indirect contact with the electrochemical cell of the sensor.

Unlike the conventional oxygen sensor which utilizes the heat of the hot exhaust gas to heat the electrochemical cell, the oxygen sensor incorporating such heating means to heat the solid electrolyte body employs a protective covering means or device which has suitable thermally insulating means for preventing the solid electrolyte body from being cooled by the cool exhaust gas immediately after the start of a cold engine. For example, the thermally insulating means may be provided by reducing the size of the gas-inlet openings formed in the covering means, or by using two covering members which form a double-walled protective covering device.

However, the conventional protective covering device used for the conventional oxygen sensor incorporating heating means is not completely satisfactory in terms of its effect on an operating response of the sensor and its effect to thermally insulate the solid electrolyte body. Namely, the operating response is deteriorated if the total area of opening in the gas-inlet portion of the covering device is excessively reduced for preventing dissipation of the heat generated by the heating means. Conversely, the effect of the thermally insulating portion of the covering device is sacrificed if the total area of opening is excessively increased for assuring a comparatively high operating response of the sensor.

SUMMARY OF THE INVENTION

It is therefore an object of the present invention to provide an improved heater-built-in sensor having a protective covering device which overcomes the above-indicated drawback of the conventional counterpart, that is, which satisfies two requirements that have been considered incompatible with each other, i.e., a sufficiently high effect of preventing dissipation or transfer of the heat generated by the heating means on the one hand, and an excellent operating response of the sensor on the other hand.

According to the present invention, there is provided a heater-built-in sensor for detecting a component in a measurement gas, comprising: (a) at least one electrochemical cell having a solid electrolyte body, and at least one pair of electrodes formed on the solid electrolyte body, the at least one pair of electrodes including a measuring electrode, the at least one electrochemical cell having a detecting portion which includes the measuring electrode; (b) heating means for heating at least the detecting portion of the at least one electrochemical cell to a predetermined operating temperature; (c) gas-inlet means for introducing the measurement gas to the measuring electrode; and (d) thermally insulating means for preventing dissipation of a heat generated by the heating means. The thermally insulating means is formed so as to surround the detecting portion such that the thermally insulating means prevents the measurement gas from flowing to or from any parts of the detecting portion, except a part at which the measuring electrode is located. The thermally insulating means is substantially separated from the gas-inlet means.

In the heater-built-in sensor of the present invention constructed as described above, the movements or flows of the measurement gas around the detecting portion of the electrochemical cell or cells are held to a minimum, while the gas-inlet portion permits a sufficiently high rate of flow of the measurement gas toward the measuring electrode, thereby assuring a sufficiently fast rate of displacement of the measurement gas adjacent the measuring electrode, and consequently a considerably improved operating response of the cell to a change in the concentration of a component of the measurement gas to be detected.

According to one advantageous feature of the invention, the gas-inlet means comprises at least one opening formed through the thermally insulating means such that the opening or openings lead to the measuring electrode. Since the required thermal insulation effect of the thermally insulating means must be achieved without lowering the operating response of the sensor, the total area of opening in the gas-inlet means must be determined so that the gas-inlet means does not provide a diffusion resistance to a flow of the measurement gas therethrough, i.e., so that the flow of the gas through the gas-inlet opening or openings is not so limited as to lower the operating response of the sensor.

According to another advantageous feature of the invention, the solid electrolyte body is generally planar in shape. In this case, the gas-inlet means for introducing the measurement gas to the measuring electrode is preferably formed locally in a suitable limited area on one of opposite major surfaces of the planar solid electrolyte body. The gas-inlet means and the thermally insulating means are so adapted that the gas-inlet means is positioned in alignment with the measuring electrode of the detecting portion, so that the thermally insulating means does not permit the flows of the measurement gas to the other parts of the detecting portion of the cell. However, the principle of the present invention may be applied to a heater-built-in sensor which uses a tubular solid electrolyte body, if the measuring electrode is formed in a limited area on the outer surface of the tubular solid electrolyte body, contrary to the conventional arrangement in which the measuring electrode is formed over substantially the entire area of the outer surface of the tubular solid electrolyte member.

According to a further advantageous feature of the invention, the thermally insulating means consists of a porous refractory material. Alternatively, the thermally insulating means may comprise portions which define a space surrounding the detecting portion.

The gas-inlet means may be provided with filter means disposed adjacent to the gas-inlet opening or openings, for preventing foreign substances contained in the measurement gas, from entering through the gas-inlet opening or openings.

According to a yet further advantageous feature of the invention, the gas-inlet means and the thermally insulating means may be provided together with means for achieving a uniform distribution of components of the measurement gas before the measurement gas is introduced through the gas-inlet means. This means for achieving the uniform distribution is disposed outwardly of the gas-inlet and thermally insulating means, so as to act on the measurement gas before the gas flows into the gas-inlet means.

According to another aspect of the invention, there is provided a heater-built-in sensor for detecting a component in a measurement gas in an external space, comprising: (a) at least one electrochemical cell having a solid electrolyte body, and at least one pair of electrodes formed on the solid electrolyte body, the at least one pair of electrodes including a measuring electrode, the at least one electrochemical cell having a detecting portion which includes the measuring electrode; (b) heating means for heating at least the detecting portion of the at least one electrochemical cell to a predetermined operating temperature; (c) diffusion-resistance means communicating with the external space and the measuring electrode, the diffusion-resistance means providing a predetermined diffusion resistance to a flow of the measurement gas therethrough; (d) gas-inlet means for introducing the measurement gas from the external space to the diffusion-resistance means; and (e) thermally insulating means for preventing dissipation of a heat generated by the heating means. The thermally insulating means, which is substantially separated from the gas-inlet means, is formed so as to surround detecting portion such that the thermally insulating means prevents the measurement gas from flowing to or from any parts of the detecting portion, except a part at which the measuring electrode is located.

The diffusion-resistance means may take any forms such as a thin flat space, a hole or aperture having a small diameter, or a porous ceramic layer, provided the diffusion-resistance means provides a predetermined diffusion resistance to a flow of the measurement gas therethrough.

According to a further aspect of the invention, there is provided a heater-built-in sensor for detecting a component in a measurement gas, comprising: (a) a sensing element comprising at least one electrochemical cell which has a solid electrolyte body, and at least one pair of electrodes formed on the solid electrolyte body, the at least one pair of electrodes including a measuring electrode exposed to the measurement gas, the sensing element having a detecting portion including the measuring electrode; (b) a heater for heating at least the detecting portion of the sensing element to a predetermined operating temperature; and (c) a protective covering device disposed so as to surround the detecting portion of the sensing element. The protective covering device includes gas-inlet means for introducing the measurement gas to the measuring electrode, and thermally insulating means for preventing dissipation of a heat generated by the heater which is substantially separated from the gas-inlet portion. The thermally insulating means, which is substantially separated from the gas-inlet means, is formed so as to surround the detecting portion such that the thermally insulating means prevents the measurement gas from flowing to or from any parts of the detecting portion, except a part at which the measuring electrode is located.

In accordance with one advantageous feature of the above aspect of the invention, the protective covering device comprises a covering member which is disposed around the detecting portion of the sensing element. The covering member has at least one gas-inlet opening which serves as the gas-inlet means. The thermally insulating means is provided in the covering member.

In one form of the above feature, the protective covering device further comprises a porous refractory member which serves as the thermally insulating means. The porous refractory member has at least one opening communicating with the at least one gas-inlet opening, and is formed so as to fill a space between the detecting portion and the covering member, except the at least one opening communicating with the at least one gas-inlet opening.

In another form of the above feature, the protective covering member includes portions which cooperate with the detecting portion to define an internal space which serves as the thermally insulating means. In this case, the portions which cooperate with the detecting portion to define an internal space may define the above-indicated at least one gas-inlet opening, and are held substantially in contact with the sensing element, so as to enclose the internal space.

According to another advantageous feature of the same aspect of the invention, the sensing element has diffusion-resistance means which communicates with the gas-inlet means and the measuring electrode. The diffusion-resistance means is formed so as to provide a predetermined diffusion resistance to a flow of the measurement gas therethrough.

In one form of the above feature of the invention, the detecting portion of the sensing element has an aperture which communicates with the diffusion-resistance means, opposite ends of the aperture being open in opposite major surfaces of the detecting portion. The gas-inlet means comprises portions defining two gas-inlet openings for introducing the measurement gas into the aperture through the opposite ends thereof.

In another form of the same feature, the diffusion-resistance means consists of two thin flat spaces formed in the detecting portion of the sensing element. The two thin flat spaces being open in opposite side surfaces of the detecting portion. The gas-inlet means comprises portions defining two gas-inlet openings for introducing the measurement gas into the two thin flat spaces.

In a further form of the same feature of the invention, the detecting portion of the sensing element has an aperture which communicates with the diffusion resistance means, one ends of the aperture being open in major surfaces of the detecting portion, the gas-inlet means comprises portions defining a gas-inlet opening for introducing the measurement gas into the aperture. In this case, the diffusion resistance means may consist of a thin flat spaces formed in the detecting portion of the sensing element.

BRIEF DESCRIPTION OF THE DRAWINGS

The above and other objects, features and advantages of the present invention will be better understood by reading the following description of preferred embodiments of the invention, when considered in conjunction with the accompanying drawings, in which:

FIG. 3(a) is a longitudinal cross sectional view showing the construction of an end portion of a conventional sensor;

FIG. 3(b) is a cross sectional view taken along line III—III of FIG. 3(a);

FIGS. 4, 6, 7, 8, 10 and 11 are fragmentary views in longitudinal cross section of other embodiments of the invention, each showing a detecting end portion of the corresponding sensor;

FIG. 5 is an exploded perspective view of the detecting end portion of the sensor of FIG. 4;

DETAILED DESCRIPTION OF THE PREFERRED EMBODIMENTS

Referring first to the cross sectional view of FIG. 1, there is shown a sensor incorporating a heater (hereinafter referred to as "heater-built-in sensor" as appropriate) according to one embodiment of the invention. The heater-built-in sensor has a sensing element 100 having a detecting portion whose essential portion is illustrated in the exploded perspective view of FIG. 2.

Figure 2:
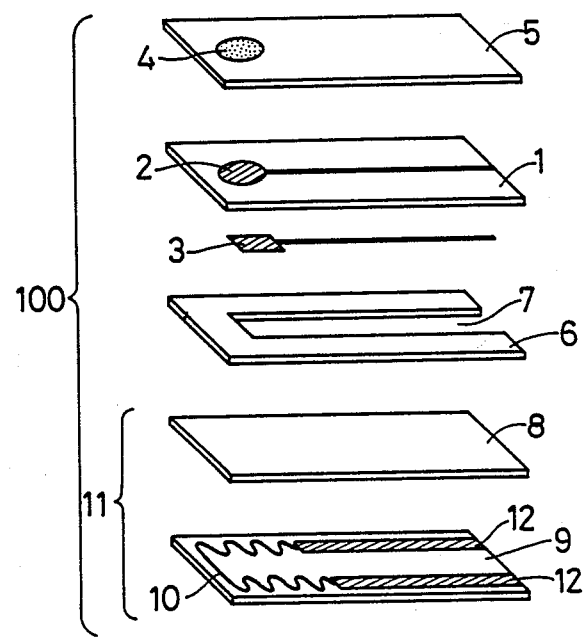
FIG. 2 is an exploded perspective view of a sensing element used in the sensor of FIG. 1.

As clearly depicted in FIG. 2, the sensing element includes a planar solid electrolyte body 1 made of zirconia ceramics containing yttria, and a porous measuring electrode 2 and a porous reference electrode 3 which are disposed on the opposite major surfaces of the planar solid electrolyte body 1. The measuring and reference electrodes 2, 3 are made of a material whose major component is platinum. The solid electrolyte body 1, and the two electrodes 2, 3 constitute an electrochemical cell which functions as an oxygen concentration cell. The porous measuring electrode 2 is covered by a porous protective layer 4 having substantially the same size as the measuring electrode 2. The porous protective layer 4 is formed of a material whose major component is spinel, for example. The entire area of the surface on which the measuring electrode 2 is formed, except the area covered by the measuring electrode 2, is covered by an air-tight layer 5 made of the same material as the solid electrolyte body 1. The porous reference electrode 3 is exposed to a cavity 7 which is defined by the solid electrolyte body 1, a spacer layer 6 made of the same material as the solid electrolyte body 1, and a ceramic layer 8 made of an electrically insulating material such as alumina. The ceramic layer 8 cooperates with another electrically insulating ceramic layer 9, to support a heating element 10 such that the two ceramic layers 8, 9 sandwich the heating element 10 therebetween. For example, the heating element 10 is made of a material consisting of 90% by weight of platinum and 10% by weight of alumina. The heating element 10 and the ceramic layers 8, 9 constitute heating means in the form of a heater layer 11. The solid electrolyte body 1, the air-tight layer 5, the spacer layer 6, and the heater layer 11, are superposed on each other so as to form the heater-built-in sensing element generally indicated at 100.

The measuring electrode 2 of the sensing element 100 is exposed to a gas to be measured (hereinafter referred to as "measurement gas"). As indicated in FIG. 1, the measurement gas reaches the surface of the measuring electrode 2, passing through an opening 14 formed in a gas-inlet portion of a cylindrical protective covering member 30, through an opening 16 formed in a thermally insulating member 15 held within the covering member 30, and through the porous protective layer 4 described above. The covering member 30 and the thermally insulating member 15 constitute a protective covering device. On the other hand, the ambient air used as a reference gas is introduced into the sensor through a vent hole 18 formed in a cap 17. The air is directed to the surface of the reference electrode 3 through a hole 20 formed in an insulating member 19 made of alumina ceramics, and through the cavity 7 formed in the sensing element 100. The measurement gas is air-tightly separated from the ambient air by a sealing glass 22 formed between the sensing element 100 and a support member 21 supporting the sensing element 100, and by a sealing member 23 disposed between the support member 21 and a housing 13 which retains the heater-built-in sensor in place. The sealing member 23 is held in pressed contact with an inner tapered surface of the housing 13, while the support member 21 is forced against the sealing member 23 with a biasing force of a spring 24, which biasing force is exerted onto the support member 21 via the insulating member 19, and a metal washer 25 interposed between the insulating member 19 and the support member 21.

The heater layer 11 as the heating means has electric terminals 12, 12 which are connected to a suitable power source to apply an electric current to the heating element 10. The energized heating element 10 generates Joule heat, whereby the sensing element 100 is heated. The protective covering device 30, 15 which surrounds the detecting end portion of the sensing element 100 has no portions that allow the measurement gas to enter into the covering member 30, except the gas-inlet opening 14, and the opening 16 in the thermally insulating member 15, and the gas-inlet opening 14. This protective covering device 30, 15 permits substantially no displacements or flows of the measurement gas within the protective covering member 30, except on the surface of the measuring electrode 2. In other words, the thermally insulating member 15 is formed so as to permit the measurement gas from the gas-inlet portion 14 to contact only the measuring electrode 2. That is, the opening 16 formed in the thermally insulating member 15 does not permit the measurement gas to contact the other portions of the sensing element 100, but permits relatively fast displacements or changes of the measurement gas adjacent to the measuring electrode 2. Accordingly, the thermally insulating member 15 serves to minimize the dissipation or transfer of the heat generated by the heater layer 11, due to the flows or movements of the measurement gas within the covering member 30, and thereby effectively utilize the heat of the heater layer 11 to heat the sensing element 100. At the same time, the gas-inlet opening 14 formed in alignment with the measuring electrode 2 is so dimentioned that the opening 14 has substantially no diffusion resistance to the flow of the measurement gas toward the measuring electrode 2, or permits the measurement gas to freely flow into the opening 16 formed in the thermally insulating member 15, for contact with the measuring electrode 2 through the porous protective layer 4. Therefore, the operating response of the sensing element 100 is also improved.

Figure 1:
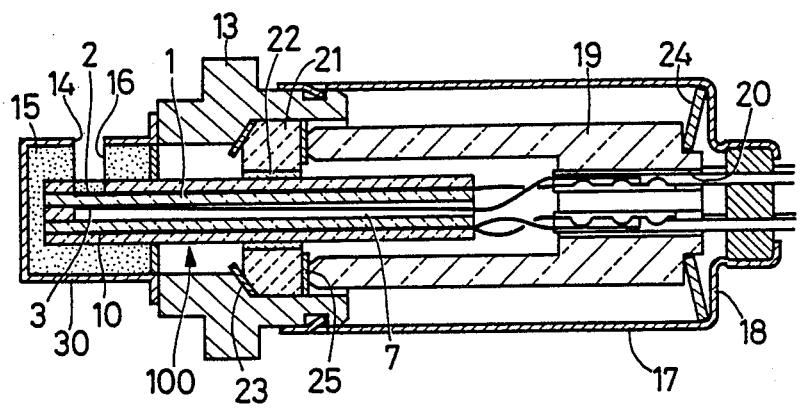
FIG. 1 is a cross sectional view of one embodiment of a heater-built-in sensor of the present invention.

The advantages of the protective covering device 30, 15 provided with the thus formed thermally insulating member 15 according to the invention will become more apparent, when the covering device 30, 15 is compared with a conventional covering device 40 as shown in FIGS. 3(a) and 3(b), wherein the same reference numerals as used in FIGS. 1 and 2 are used to identify the corresponding parts.

More specifically, the conventional covering device 40 has cylindrical outer and inner covering members 32, 34. Each of these two covering members 32, 34 has a plurality of gas-inlet openings 14, for example, six gas-inlet openings 14 that are evenly spaced from each other in the circumferential direction of the covering member 32, 34. As indicated in FIG. 3(b), the openings 14 in the outer covering member 32 are displaced by 30 degrees relative to the openings 14 in the inner covering member 34, in the circumferential direction of the members 32, 34, so that the two covering members 32, 34 provide thermally insulating portions 15 for preventing a transfer of the heat generated by heating means of a sensing element 100, by the measuring gas flowing through the gas-inlet openings 14.

As indicated above, the conventional protective covering device 40 has the gas-inlet openings 14 at a plurality of positions, and the thermally insulating portions 15 and the gas-inlet portions 14 are not separated from each other. Therefore, the measurement gas may flow to and from any parts of the sensing element 100. According to this arrangement, the effect of the thermally insulating portions 15 to prevent the heat transfer due to the movements of the measurement gas will be lowered, if the gas-inlet openings 14 are enlarged to increase a rate of flow of the measurement gas through the thermally insulating portions 15, or to increase a rate of displacement of the measurement gas adjacent the measuring electrode 2, for the purpose of enhancing an operating response of the sensing element to a change in the measurement gas. This reduced effect of the thermally insulating portions 15 has a particularly unfavorable effect on the operation of the sensing element 100, especially while the temperature of the measurement gas is low and the sensing element should be heated by the built-in heater to its operating temperature. On the other hand, if the size or number of the gas-inlet openings 14 is reduced for increasing the effect of the thermally insulating portions 15, the rate of flow of the measurement gas through the openings 14 toward the measuring electrode 2 is limited, resulting in lowering the rate of displacement of the measurement gas adjacent the measuring electrode, and consequently lowering the operating response of the sensing element 100.

While zirconia ceramics containing yttria is used for the solid electrolyte members 1, 5, 6 in the illustrated embodiment of FIGS. 1 and 2, it is possible to use $\beta$-alumina, aluminum nitride, NASICON, $SrCeO_3$, solid solution of $Bi_2O_3$ and rare earth oxides, $La_{1-x}Ca_x$-$YO_{3-\alpha}$. Further, the ceramic layers 8, 9 of the heater layer 11 may be made of spinel, mullite, zircon or other ceramic materials, as well as alumina.

The measuring and reference electrodes 2, 3 may be formed by a suitable known method, for example, by screen printing, sputtering or vapor deposition. If the screen printing technique is used, a paste for the electrodes 2, 3 is prepared by adding known binder and solvent to a powder mixture of Pt, Pd, Rh or other metals of the platinum group, and a solid electrolyte material such as zirconia. The prepared paste is applied to the unfired or fired planar solid electrolyte body 1, in the form of layers which are eventually fired into the electrodes 2, 3.

The material for the heating element 10 may be a refractory metal such as Pt, Mo, W, Ni or Cr, or an alloy including these refractory metals, or a mixture of at least one of these metals and a ceramic material such as zirconia, spinel or alumina. Like the electrodes 2, 3, the heating element 10 may be formed by screen printing, sputtering, vapor deposition, or other suitable known methods.

The thermally insulating member 15 of the present heater-built-in sensor may be made of a known refractory material such as alumina, silica, zirconia, magnesia, calcia, SiC, $Fe_2O_3$ or $Cr_2O_3$, or a porous metal, or alternatively a multilayered metal sheet. Preferably, the thermally insulating member 15 has a suitable porosity so that the insulating portion 15 may not act as a heat-sink for the heat generated by the heater layer 11.

The protective covering device 30, 15 of FIG. 1 may be replaced by any one of modified arrangements illustrated in FIGS. 4–8 and 10–12.

The arrangement illustrated in FIG. 4 is characterized by the shape of the opening 16 formed in the thermally insulating member 15. Described more specifically, a cylindrical protective covering member 50 of FIG. 4 has a gas-inlet opening 14 which communicates with the opening 16. The opening 16 has a straight portion 16a of a relatively small diameter adjacent to the gas-inlet opening 14, and a coned portion 16b whose diameter increases in the direction from the straight portion 16a toward the sensing element 100. In this arrangement, the gas-inlet opening 14 and the straight portion 16a of the opening 16 are adapted to permit only a required minimum rate of flow of the measurement gas therethrough toward the measuring electrode of the sensing element 100. Stated differently, the size of the gas-inlet portion consisting of the gas-inlet opening 14 and the straight portion 16a is minimized to such an extent just below a level at which the opening 14 starts providing a resistance to the flow of the measurement gas. The thermally insulating member 15 defining the opening 16 can effectively prevent the dissipation of the heat generated by the heater layer incorporated in the sensing element 100.

FIG. 5 shows in detail the construction of the protective covering device of FIG. 4. The cylindrical protective covering member 50 consists of two halves 52, 52. The thermally insulating member 15 consists of two halves 15', 15' which have a generally semi-circular cross sectional shape. Each of the two halves 15', 15' of the insulating member 15 has a rectangular groove 48. The two grooves 48 in the two halves 15', 15' cooperate to define a slot in which the detecting portion of the rectangular sensing element 100 is received. The two halves 52, 52 of the covering member 50 are made of a refractory metal such as SUS304. The assembly of the sensing element 100 and the thermally insulating member 15 is enclosed by the two halves 52, 52, which are welded to each other so as to clamp the two halves 15', 15' of the insulating member 15 with the sensing element 100 held therebetween.

Figure 6:
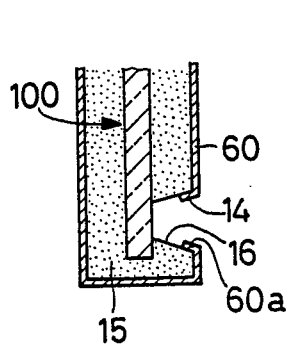

The protective covering device shown in FIG. 6 is characterized by the gas-inlet opening 14 formed in a cylindrical protective covering member 60. More specifically, the gas-inlet opening 14 is defined by a inwardly bent portion 60a of the covering member 60. The bent portion 60a is held in contact with the outer end portion of the surface of the thermally insulating member 15 that defines the opening 16. The bent portion 60a thus serves to retain the refractory insulating member 15.

Figure 7:
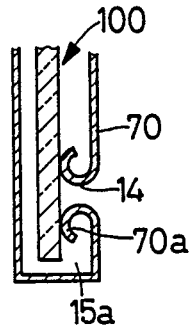

The protective covering device shown in FIG. 7 is different from those of FIGS. 1, 4 and 6, in that a thermally insulating member is not used. That is, the protective covering device of FIG. 7 consists of a cylindrical covering member 70 which has an internal space 15a serving as thermally insulating means. The covering member 70 has an inwardly curved portion 70a which defines the gas-inlet opening 14. It is preferred that the curved portion 70a is held in contact with the corresponding surface of the sensing element 100, as indicated in FIG. 7. In this case, it is advantageous that the curved portion 70a has a relatively small thickness, in order to prevent the curved portion 70a from acting as a heatsink. However, it is not essential to hold the curved portion 70a in contact with the surface of the sensing element 100. However, the gap between the sensing element 100 and the curved portion 70a must be so small that the flow of the measurement gas through the gap is almost negligible, as compared with the flow of the gas through the gas-inlet opening 14.

Figure 8:
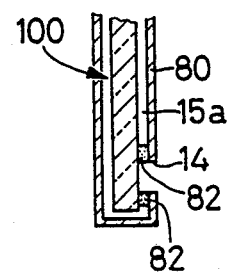

The protective covering device shown in FIG. 8 is a modification of that of FIG. 7. This modified covering device is characterized by a covering member 80 which has a square cross sectional shape, and a refractory thermally insulating member 82 provided in the covering member 80. The sensing element 100 is received in the square covering member 80 such that the four inner surfaces of the covering member 80 face to the corresponding four outer surfaces of the sensing element 100, with suitable distances therebetween, so as to define an internal space 15a which cooperates with the insulating member 82 to provide thermally insulating means. The thermally insulating member 82 is disposed between the portion of the covering member 80 adjacent to the gas-inlet opening 14, and the surface of the sensing element 100. This arrangement does not suffer from a problem that the portion of the covering member 80 defining the opening 14 tends to act as a heatsink. Further, the present arrangement permits easy formation of the thermally insulating member 82.

Figure 9:
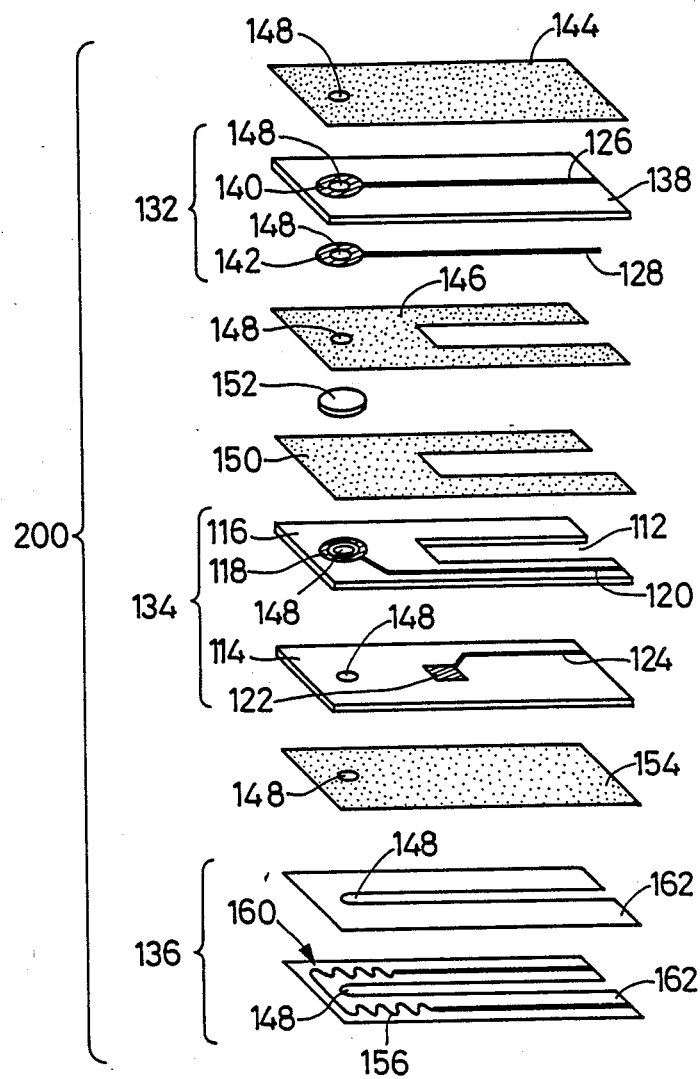
FIG. 9 is an exploded perspective view of a modified form of a sensing element of a sensor according to the invention.

Referring next to an exploded perspective view of FIG. 9, there is shown another heater-built-in sensing element 200 which may be used in place of the sensing element 100 of FIG. 2.

The sensing element 200 includes a first planar solid electrolyte body 138, and a first and a second annular pumping electrode 140, 142 formed on the opposite major surfaces of the first solid electrolyte body 138. The first and second pumping electrodes 140, 142 are covered by respective protective layers 144, 146 which are disposed so as to also cover the corresponding surfaces of the solid electrolyte body 138, either totally or partially. The first solid electrolyte body 138 and the pumping electrodes 40, 142 constitute an electrochemical pumping cell 132. The sensing element 200 further includes a second planar solid electrolyte body 116, a third solid electrolyte body 114, a measuring electrode 118 formed on the second solid electrolyte body 116, a reference electrode 122 formed on the third solid electrolyte body 114, and a protective layer 150 covering the measuring electrode 118 and the second solid electrolyte body 116. The second and third solid electrolyte bodies 116, 114 and the measuring and reference electrodes 118, 122 constitute an electrochemical sensing cell 134. Between the two electrochemical cells 132, 134, there is formed diffusion-resistance means in the form of a thin flat space indicated at 152 for illustrative purpose. Reference numeral 112 designates a cavity which communicates with the atmosphere. The reference electrode 122 is disposed so that it is exposed to the air in the cavity 112. Reference numerals 120, 124, 126 and 128 designate electrical leads connected to the electrodes 118, 122, 140 and 142, respectively.

On one side of the sensing cell 134 remote from the pumping cell 132, there is provided a heater layer 136 which consists of a heating element 156, and two airtight ceramic layers 162, 162 which support the heating element 156 therebetween. An electrically insulating layer 154 is disposed between the sensing cell 134 and the heater layer 136.

The above-indicated layers or members are all superposed on each other to form a laminar structure, as indicated in FIG. 9, and co-fired into the heater-built-in sensing element 200. The sensing element 200 has a detecting portion which has an aperture 148 for introducing the measurement gas in the external space, into the thin flat space 152. The aperture 148 is formed through the thickness of the laminar structure of the sensing element 200.

As described above, the sensing element 200 incorporates the pumping cell 132 as well as the sensing cell 134. Since the operating temperature of the pumping cell 132 is higher than that of the electrochemical cell shown in FIG. 2, the thermally insulating effect of the protective covering device of the sensor has an increased importance to the operation of the sensor.

In operation of the heater-built-in sensing element 200, the measurement gas introduced in the thin flat space 152 which acts as diffusion resistance means is controlled by means of a pumping action of the pumping cell 132, and the thus controlled atmosphere is detected by the sensing cell 134. In the case where the sensing element 200 is used as an oxygen sensor for detecting an exhaust gas produced by an internal combustion engine, for example, the sensing element 200 serves as so-called "lean-burned sensor" if the exhaust gas produced by the engine has a higher oxygen concentration than the exhaust gas which is produced at a stoichiometric air/fuel (A/F) ratio of the air-fuel mixture. In this case, oxygen in the atmosphere in the thin flat space 152 is pumped out toward the first pumping electrode 140, by the pumping cell 132, so that the oxygen concentration of the atmosphere in the thin flat space 152 is held lower than that of the exhaust gas produced by the engine. If the exhaust gas to be detected contains a relatively large amount of unburned fuel, the sensing element 200 operates as so-called "rich burned sensor" in which the oxygen concentration of the atmosphere in the thin flat space 152 is held higher than that of the exhaust gas, by the pumping cell 132. More specifically, the pumping cell 132 operates to pump the residual oxygen in the exhaust gas, or oxygen obtained by decomposition of the oxides in the exhaust gas, into the thin flat space 152. Of course, like the sensing element 100 of FIG. 2, the sensing element 200 is capable of dealing with the exhaust gas which is produced as a result of an air-fuel mixture having the stoichiometric air/fuel ratio.

Figure 10:
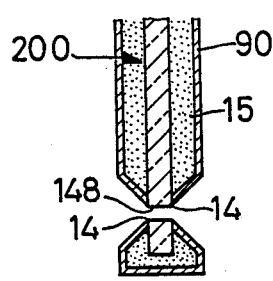
Figure 11:
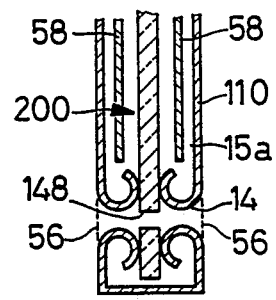

While the sensing element 200 may be adapted to employ the protective covering device including the covering member 30, 50, 60, 70 or 80, a protective covering device as shown in FIG. 10 or FIG. 11 may be suitably used since the sensing element 200 has the aperture 148.

The protective covering device of FIG. 10 utilizes the basic structural concept of the device of FIG. 6, but is different from the device of FIG. 6. Described in more detail, the covering device of FIG. 10 uses a protective covering member 90 having two opposed gas-inlet openings 14 which are formed on the opposite sides of the sensing element 200, such that the two openings 14 are aligned with the open ends of the aperture 148. This arrangement facilitates the flow of the measurement gas into the thin flat space 152 through the aperture 148 formed in the sensing element 200, thereby contributing to improvement in the operating response of the element 200.

The protective covering device of FIG. 10 may be replaced by the protective covering device illustrated in FIG. 11. This modified covering device of FIG. 11 utilizes the basic structural concept of the device of FIG. 7. While the device of FIG. 11 uses two gas-inlet openings 14 like the device of FIG. 10, the two openings 14 are defined by curved bent portions of a covering member 110, as in the embodiment of FIG. 7. In addition, each of the openings 14 is provided with a filter 56 for preventing entry of dirt and dust, metal particles or other foreign substances contained in the measurement gas, into the opening 14. The filter 56 has a porosity that provides substantially no diffusion resistance to the flow of the gas. Further, the protective covering member 110 has a refractory metal member 58 disposed in an internal space 15a. This refractory metal member 58 cooperates with the space 15a to constitute thermally insulating means. The filter 56 may be formed of a metal plate having small holes, or a porous ceramic body having a larger porosity than a material that is used for the thermally insulating member according to the invention.

Figure 14:
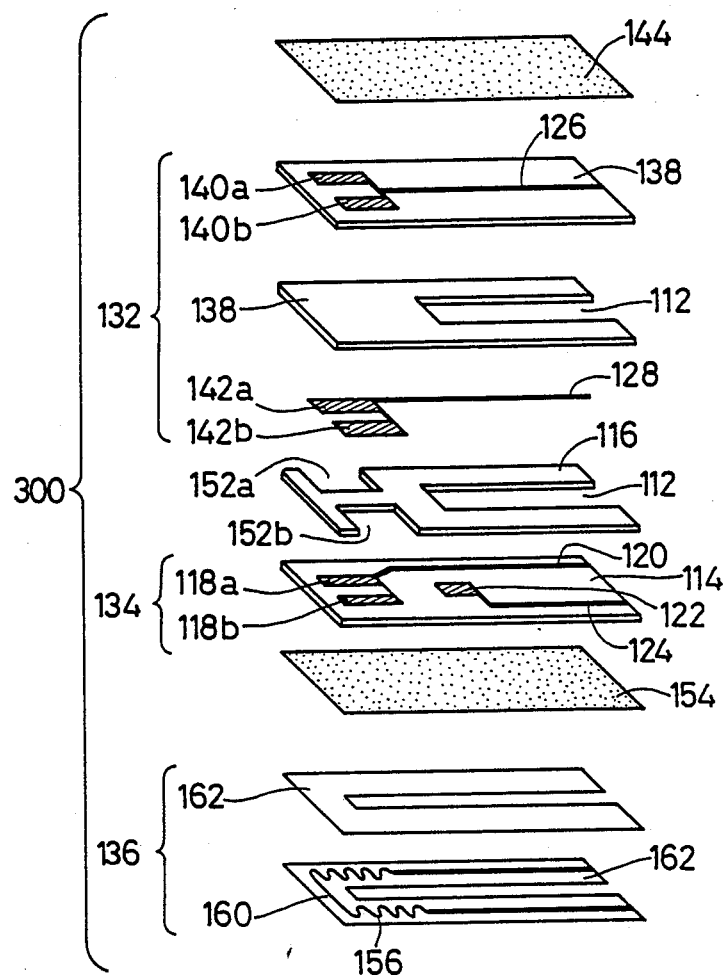
FIG. 14 is an exploded perspective view of a sensing element of a sensor according to yet another embodiment of the invention.
Figure 15:
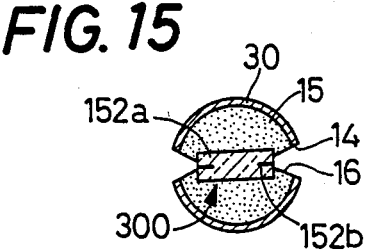
FIG. 15 is a transverse cross sectional view of the sensor of FIG. 14.

The sensing element 200 of FIG. 9 may be replaced by a modified sensing element 300 shown in FIG. 14, which uses two rectangular thin flat spaces 152a, 152b formed in the solid electrolyte body 116. These two thin flat spaces 152a, 152b are open in the opposite side surfaces of the sensing element 300 which are perpendicular to the plane of the solid electrolyte body 116. In this case, second pumping electrode 142a, 142b and measuring electrode 118a, 118b are exposed to the thin flat spaces 152a, 152b, as indicated in the figure. The detecting portion of the sensing element 300 may be protected by a protective covering device 30, 15 shown in FIG. 15. This covering device has two opposite gas-inlet openings 14, 14 formed in a covering member 30, and two opposite openings 16 formed in a thermally insulating member 15 provided between the covering member 30 and the sensing element 300. The openings 16 are aligned with the opposite side surfaces of the sensing element 300 in which the thin flat spaces 152a, 152b are open. The two gas-inlet openings 14 and the two openings 16 cooperate to direct the measurement gas to the thin flat spaces 152a, 152b.

While the illustrated protective covering devices use a single protective covering member in which a thermally insulating means is provided, it is possible to use another covering member disposed around the covering member having the thermally insulating means. For example, such an outer covering member may be used for achieving uniform distribution of components of the measurement gas before the gas is introduced into the inner covering member through the gas-inlet means. In this case, the outer covering member may have a plurality of openings which have substantially no resistance to the flow of the gas therethrough.

Figure 12:
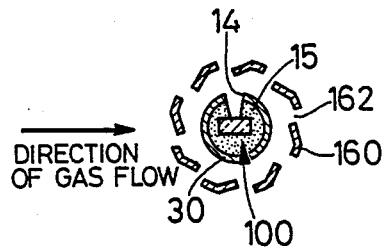
FIG. 12 is a transverse cross sectional view of a detecting end portion of a sensor according to a further embodiment of the present invention.

An example of a protective covering device using such an outer covering member is shown in the transverse cross sectional view of FIG. 12. In this device, an outer covering member 160 is disposed radially outwardly of the inner covering member 30, and has a plurality of elongate slots 162 which extend in the axial direction of the cylindrical inner covering member 30. The elongate slots 162 are spaced from each other in the circumferential direction of the outer covering member 160. The outer covering member 160 having the elongate slots 162 has substantially no thermal insulation effect. However, the elongate slots 162 have a function of changing the direction of flow of the measurement gas relative to the sensing element 100. In this arrangement, the measurement gas is introduced to the sensing element 100 through the gas-inlet opening 14 of the inner covering member 30, after the measurement gas is introduced into the outer covering member 160.

Figure 13:
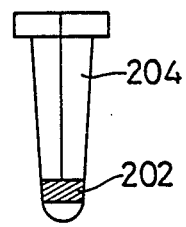
FIG. 13 is a front elevational view of a tubular sensing element of a sensor according to a still further embodiment of the invention.

While the heater-built-in sensors which have been illustrated use a planar sensing element, the principle of the present invention may be applied to a sensor using a tubular sensing element. In this case, the measuring electrode is formed in a limited area of the outer surface of a tubular solid electrolyte body 104, as indicated at 202 in FIG. 13. The detecting portion of the tubular sensing element including the measuring electrode 202 may be suitably protected by a covering device which has gas-inlet portion substantially aligned with the measuring electrode 202, according to the concept of the invention. In this tubular heater-built-in sensor, too, the covering device provides a thermal insulation effect, and ensures a sufficiently high rate of displacement of the measurement gas and consequently excellent operating response of the sensing element.

Further, the principle of the invention is applicable to a heater-built-in sensor which uses a sensing element utilizing $TiO_2$ or other materials whose electrical resistance is varied when exposed to the measurement gas.

The features and advantages of the present invention will be readily understood from the following experiments:

EXPERIMENT 1

The heater-built-in sensor of FIGS. 1 and 2 was tested in terms of its response time and the power consumption by the heater layer 11. More specifically, the detecting portion of the sensor was exposed to a 300° C. gas produced by a propane gas burner. The composition of the air-fuel mixture was changed so that the air/fuel ratio of the mixture was changed from 14 to 15. The time required for the sensor to detect this change was measured as the response time. Further, the electric energy required to heat the detecting portion of the sensor to 500° C. was measured. The measurements are indicated in Table 1, together with the comparative values of a conventional sensor with a protective covering device consisting of the outer covering member 32 of FIGS. 3(a) and 3(b). The response time measured is a length of time between the moment when the solenoid valve was activated to change the amount of the fuel gas, and the moment when the electromotive force induced in the sensor was reduced to one half of the full variation width.

TABLE 1

|  | Response Time | Heater Power |
|---|---|---|
| Sensor of the Invention | 250 msec | 3 w |
| Conventional Sensor | 310 msec | 4 w |

As indicated in Table 1, the sensor according to the invention exhibited better results in both of the operating response and the thermal insulation effect.

EXPERIMENT 2

The heater-built-in sensor which uses the sensing element of FIG. 9 and the protective covering device of FIG. 10 was tested in the 300° C. gas of the propane gas burner, in terms of the response time upon change of the air/fuel ratio from 14 to 15, and the electric energy necessary to heat the detecting portion of the heating element to 700° C. The measurements are indicated in Table 2. The same tests were conducted on a conventional sensor using the protective covering device of FIGS. 3(a) and 3(b).

TABLE 2

|  | Response Time | Heater Power |
|---|---|---|
| Sensor of the Invention | 370 msec | 6 w |
| Conventional Sensor | 680 msec | 10 w |

As is apparent from Table 2, the sensor according to the invention exhibited improved operating response and thermal insulation effect. Further, Experiment 2 confirmed that the protective covering device according to the invention was particularly effective when the detecting portion was maintained at a comparatively high temperature by the built-in heater. As in Experiment 1, the response time was obtained by measuring a time between the moment of activation of the solenoid valve to change the fuel amount, and the moment when the pump current was reduced to one half of the full variation width.

While the present invention has been described in its preferred embodiments with some degree of particularity, it is to be understood that the invention is not limited thereto, but various changes and modifications may be made in the invention, without departing from the spirit and scope of the invention defined in the following claims.

What is claimed is:

1. A heater-built-in sensor for detecting a component in a measurement gas, comprising:

at least one electrochemical cell having a solid electrolyte body, and at least one pair of electrodes formed on said solid electrolyte body, said at least one pair of electrodes including a measuring electrode, said at least one electrochemical cell having a detecting portion which includes said measuring electrode, said at least one electrochemical cell being exposed to said measurement gas at said detecting portion;

heating means for heating at least said detecting portion of said at least one electrochemical cell to a predetermined operating temperature; and a protective covering device surrounding said detecting portion of said at least one electrochemical cell and said heating means, said protective covering device comprising gas inlet means for introducing the measurement gas to said measuring electrodes, and thermally insulating means for preventing dissipation of heat generated from said heating means, wherein said thermally insulating means and said gas inlet means are separate structures, said thermally insulating means surrounding and contacting said detecting portion at all parts of said detecting portion, except a part at which said measuring electrode is located.

2. The heater-built-in sensor of claim 1, wherein said gas-inlet means comprises at least one opening formed through said thermally insulating means such that said at least one opening leads to said measuring electrode.

3. The heater-built-in sensor of claim 2, further comprising a filter disposed adjacent to said at least one opening, for preventing foreign substances contained in the measurement gas, from entering into said at least one opening.

4. The heater-built-in sensor of claim 1, wherein said solid electrolyte body is generally planar in shape.

5. The heater-built-in sensor of claim 1, wherein said thermally insulating means consists of a porous refractory material.

6. The heater-built-in sensor of claim 1, wherein said thermally insulating means comprises portions defining a space surrounding said detecting portion.

7. The heater-built-in sensor of claim 1, further comprising means disposed around said gas-inlet means and said thermally insulating means, for achieving a uniform distribution of components of the measurement gas before the measurement gas is introduced through said gas-inlet means.

8. A heater-built-in sensor for detecting a component in a measurement gas in an external space, comprising:

at least one electrochemical cell having a solid electrolyte body, and at least one pair of electrodes formed on said solid electrolyte body, said at least one pair of electrodes including a measuring electrode, said at least one electrochemical cell having a detecting portion which includes said measuring electrode, said at least one electrochemical cell being exposed to said measurement gas at said detecting portion;
heating means for heating at least said detecting portion of said at least one electrochemical cell to a predetermined operating temperature;
diffusion-resistance means communicating with said external space and said measuring electrode, said diffusion-resistance means providing a predetermined diffusion resistance to a flow of the measurement gas therethrough; and
a protective covering device surrounding said detecting portion of said at least one electrochemical cell, said heating means, and said diffusion-resistance means;
wherein said protective covering device includes a gas inlet means for introducing the measurement gas to said diffusion-resistance means and thermally insulating means for preventing dissipation of heat generated from said heating means, wherein said thermally insulating means and said gas inlet means are separate structures, said thermally insulating means surrounding and contacting said detecting portion at all parts of said detecting portion, except a part at which said measuring electrode is located.

9. The heater-built-in sensor of claim 8, wherein said gas-inlet means comprises at least one opening formed through said thermally insulating means such that said at least one opening leads to said measuring electrode.

10. The heater-built-in sensor of claim 9, further comprising a filter disposed adjacent to said at least one opening, for preventing foreign substances contained in the measurement gas, from entering into said at least one opening.

11. The heater-built-in sensor of claim 8, wherein said solid electrolyte body is generally planar in shape.

12. The heater-built-in sensor of claim 8, wherein said thermally insulating means consists of a porous refractory material.

13. The heater-built-in sensor of claim 8, wherein said thermally insulating means comprises portions defining a space surrounding said detecting portion.

14. The heater-built-in sensor of claim 8, further comprising means disposed around said gas-inlet means and said thermally insulating means, for achieving a uniform distribution of components of the measurement gas before the measurement gas is introduced through said gas-inlet means.

15. A heater-built-in sensor for detecting a component in a measurement gas, comprising:
a sensing element comprising at least one electrochemical cell having a solid electrolyte body, and at least one pair of electrodes formed on said solid electrolyte body, said at least one pair of electrodes including a measuring electrode exposed to the measurement gas, said at least one electrochemical cell having a detecting portion which includes said measuring electrode, said at least one electrochemical cell being exposed to said measurement gas at said detecting portion;
a heater for heating at least said detecting portion of said at least one electrochemical cell to a predetermined operating temperature; and
a protective covering device surrounding said detecting portion of said sensing element and said heater, said protective covering device including:
(a) gas-inlet means for introducing the measurement gas to said measuring electrode, and
(b) thermally insulating means for preventing dissipation of heat generated from said heater, wherein said thermally insulating means and said gas inlet means are separate structures, said thermally insulating means surrounding and contacting said detecting portion at all parts of said detecting portion, except a part at which said measuring electrode is located.

16. The heater-built-in sensor of claim 15, wherein said protective covering device comprises a covering member which is disposed around said detecting portion of said sensing element, said covering member having at least one gas-inlet opening which serves as said gas-inlet means, said thermally insulating means being provided in said covering member.

17. The heater-built-in sensor of claim 16, wherein said protective covering device further comprises a porous refractory member which serves as said thermally insulating means, said porous refractory member having at least one opening communicating with said at least one gas-inlet opening, said porous refractory member filling a space between said detecting portion and said covering member, except said at least one opening communicating with said at least one gas-inlet opening.

18. The heater-built-in sensor of claim 16, wherein said protective covering member includes portions which cooperate with said detecting portion to define an internal space which serves as said thermally insulating means.

19. The heater-built-in sensor of claim 18, wherein said portions which cooperate with said detecting portion to define an internal space define said at least one gas-inlet opening, and are held substantially in contact with said sensing element, so as to enclose said internal space.

20. The heater-built-in sensor of claim 15, wherein said sensing element has diffusion-resistance means which communicates with said gas-inlet means and said measuring electrode, said diffusion-resistance means providing a predetermined diffusion resistance to a flow of the measurement gas therethrough.

21. The heater-built-in sensor of claim 20, wherein said detecting portion of the sensing element has an aperture which communicates with said diffusion-resistance means, opposite ends of said aperture being open in opposite major surfaces of said detecting portion, said gas-inlet means comprising portions defining two gas-inlet openings for introducing the measurement gas into said aperture through said opposite ends thereof.

22. The heater-built-in sensor of claim 21, wherein said diffusion resistance means consists of a thin flat spaces formed in said detecting portion of said sensing element.

23. The heater-built-in sensor of claim 20, wherein said diffusion-resistance means consists of two thin flat spaces formed in said detecting portion of said sensing element, said two thin flat spaces being open in opposite side surfaces of said detecting portion, said gas-inlet means comprising portions defining two gas-inlet openings for introducing the measurement gas into said two thin flat spaces.

24. The heater-built-in sensor of claim 20, wherein said detecting portion of the sensing element has an aperture which communicates with said diffusion resistance means, one of opposite ends of said aperture being open in one of major surfaces of said detecting portion, said gas-inlet means comprising portions defining a gas-inlet opening for introducing the measurement gas into said aperture.

25. A heater-built-in sensor for detecting a component in a measurement gas, comprising:
   at least one electrochemical cell having a solid electrolyte body, and at least one pair of electrodes formed on said solid electrolyte body, said at least one pair of electrodes including a measuring electrode, said at least one electrochemical cell having a detecting portion which includes said measuring electrode, said at least one electrochemical cell being exposed to said measurement gas at said detecting portion;
   heating means for heating at least said detecting portion of said at least one electrochemical cell to a predetermined operating temperature; and
   a protective covering device surrounding said detecting portion of said at least one electrochemical cell and said heating means;
   said protective covering device including a protective covering member having at least one opening which provides a gas inlet means for introducing the measurement gas solely to said measuring electrode and thermally insulating means for preventing dissipation of heat generated from said heating means, wherein said thermally insulating means and said gas inlet means are separate structures, said thermally insulating means surrounding and contacting said detecting portion at all parts of said detecting portion, except a part at which said measuring electrode is located.

26. The heater-built-in sensor of claim 25, wherein said gas-inlet means comprises at least one opening formed through said thermally insulating means such that said at least one opening leads to said measuring electrode.

27. The heater-built-in sensor of claim 26, further comprising a filter disposed adjacent to said at least one opening, for preventing foreign substances contained in the measurement gas, from entering into said at least one opening.

28. The heater-built-in sensor of claim 25, wherein said solid electrolyte body is generally planar in shape.

29. The heater-built-in sensor of claim 25, wherein said thermally insulating means consists of a porous refractory material.

30. The heater-built-in sensor of claim 25, wherein said thermally insulating means comprises portions defining a space surrounding said detecting portion.

31. The heater-built-in sensor of claim 25, further comprising means disposed around said gas-inlet means and said thermally insulating means, for achieving a uniform distribution of components of the measurement gas before the measurement gas is introduced through said gas-inlet means.

32. A heater-built-in sensor for detecting a component in a measurement gas in an external space, comprising:
   at least one electrochemical cell having a solid electrolyte body, and at least one pair of electrodes formed on said solid electrolyte body, said at least one pair of electrodes including a measuring electrode, said at least one electrochemical cell having a detecting portion which includes said measuring electrode, said at least one electrochemical cell being exposed to said measurement gas at said detecting portion;
   heating means for heating at least said detecting portion of said at least one electrochemical cell to a predetermined operating temperature;
   diffusion-resistance means communicating with said external space and said measuring electrode, said diffusion-resistance means providing a predetermined diffusion resistance to a flow of the measurement gas therethrough; and
   a protective covering device surrounding said detecting portion of said at least one electrochemical cell, said heating means and said diffusion-resistance means;
   said protective covering device includes a protective covering member having at least one opening which provides a gas-inlet means for introducing the measurement gas solely to said measuring electrode through diffusion-resistance means and thermally insulating means for preventing dissipation of heat generated from said heating means, wherein said thermally insulating means and said gas inlet means are separate structures, said thermally insulating means surrounding and contacting said detecting portion at all parts of said detecting portion, except a part at which said measuring electrode is located.

33. The heater-built-in sensor of claim 32, wherein said gas-inlet means comprises at least one opening formed through said thermally insulating means such that said at least one opening leads to said measuring electrode.

34. The heater-built-in sensor of claim 33, further comprising a filter disposed adjacent to said at least one opening, for preventing foreign substances contained in the measurement gas, from entering into said at least one opening.

35. The heater-built-in sensor of claim 32, wherein said solid electrolyte body is generally planar in shape.

36. The heater-built-in sensor of claim 32, wherein said thermally insulating means consists of a porous refractory material.

37. The heater-built-in sensor of claim 32, wherein said thermally insulating means comprises portions defining a space surrounding said detecting portion.

38. The heater-built-in sensor of claim 32, further comprising means disposed around said gas-inlet means and said thermally insulating means, for achieving a uniform distribution of components of the measurement gas before the measurement gas is introduced through said gas-inlet means.

39. A heater-built-in sensor for detecting a component in a measurement gas, comprising:
   a sensing element comprising at least one electrochemical cell having a solid electrolyte body, and at least one pair of electrodes formed on said solid electrolyte body, said at least one pair of electrodes including a measuring electrode exposed to the measurement gas, said at least one electrochemical cell having a detecting portion which includes said measuring electrode, said at least one electrochemical cell being exposed to said measurement gas at said detecting portion;
   a heater for heating at least said detecting portion of said at least one electrochemical cell to a predetermined operating temperature; and
   a protective covering device surrounding said detecting portion of said sensing element and said heater, said protective covering device including:

(a) a protective covering member having at least one opening which provides a gas-inlet means for introducing the measurement gas solely to said measuring electrode, and (b) thermally insulating means for preventing dissipation of heat generated from said heater, wherein said thermally insulating means and said gas inlet means are separate structures, said thermally insulating means surrounding and contacting said detecting portion at all parts of said detecting portion, except a part at which said measuring electrode is located.

40. The heater-built-in sensor of claim 39, wherein said protective covering device comprises a covering member which is disposed around said detecting portion of said sensing element, said covering member having at least one gas-inlet opening which serves as said gas-inlet means, said thermally insulating means being provided in said covering member.

41. The heater-built-in sensor of claim 40, wherein said protective covering device further comprises a porous refractory member which serves as said thermally insulating means, said porous refractory member having at least one opening communicating with said at least one gas-inlet opening, said porous refractory member filling a space between said detecting portion and said covering member, except said at least one opening communicating with said at least one gas-inlet opening.

42. The heater-built-in sensor of claim 40, wherein said protective covering member includes portions which cooperate with said detecting portion to define an internal space which serves as said thermally insulating means.

43. The heaterbuilt-in sensor of claim 42, wherein said portions which cooperate with said detecting portion to define an internal space define said at least one gas-inlet opening, and are held substantially in contact with said sensing element, so as to enclose said internal space.

44. The heater-built-in sensor of claim 39, wherein said sensing element has diffusion-resistance means which communicated with said gas-inlet means and said measuring electrode, said diffusion-resistance means providing a predetermined diffusion resistance to a flow of the measurement gas therethrough.

45. The heater-built-in sensor of claim 44, wherein said detecting portion of the sensing element has an aperture which communicates with said diffusion-resistance means, opposite ends of said aperture being open in opposite major surfaces of said detecting portion, said gas-inlet means comprising portions defining two gas-inlet openings for introducing the measurement gas into said aperture through said opposite ends thereof.

46. The heater-built-in sensor of claim 45, wherein said diffusion resistance means consists of thin flat spaces formed in said detecting portion of said sensing element.

47. The heater-built-in sensor of claim 44, wherein said diffusion-resistance means consists of two thin flat spaces formed in said detecting portion of said sensing element, said two thin flat spaces being open in opposite side surfaces of said detecting portion, said gas-inlet means comprising portions defining two gas-inlet openings for introducing the measurement gas into said two thin flat spaces.

48. The heater-built-sensor of claim 44, wherein said detecting portion of the sensing element has an aperture which communicates with said diffusion resistance means, one of opposite ends of said aperture being open in one of major surfaces of said detecting portion, said gas-inlet means comprising portions defining a gas-inlet opening for introducing the measurement gas into said aperture.

* * * * *